United States Patent
Reid et al.

[11] Patent Number: 6,077,863
[45] Date of Patent: Jun. 20, 2000

[54] 2-ARYL-4-HALO-5-(TRIFLUOROMETHYL) PYRROLE-3-CARBONITRILES FOR THE PROTECTION OF WOOD, WOOD PRODUCTS AND WOODEN STRUCTURES FROM INSECT ATTACK

[75] Inventors: Byron L. Reid, Langhorne; Robert A. Farlow, Newtown, both of Pa.

[73] Assignee: American Cyanamid Company, Madison, N.J.

[21] Appl. No.: 09/130,978

[22] Filed: Aug. 7, 1998

Related U.S. Application Data

[60] Provisional application No. 60/055,054, Aug. 8, 1997.

[51] Int. Cl.[7] .................. A01N 43/36; C07D 207/416
[52] U.S. Cl. .................. 514/428; 514/427; 514/429; 548/560; 548/561; 548/562
[58] Field of Search .................. 514/427, 429, 514/428; 548/560, 562, 561

[56] References Cited

U.S. PATENT DOCUMENTS

| | | | |
|---|---|---|---|
| 4,857,651 | 8/1989 | Brown et al. | 549/443 |
| 5,010,098 | 4/1991 | Brown et al. | 514/426 |
| 5,118,702 | 6/1992 | Wollweber et al. | 514/409 |
| 5,233,051 | 8/1993 | Uhr et al. | 548/526 |
| 5,233,052 | 8/1993 | Kuhn et al. | 548/557 |
| 5,310,938 | 5/1994 | Brown et al. | 548/557 |
| 5,378,724 | 1/1995 | Uhr et al. | 514/424 |
| 5,455,263 | 10/1995 | Doscher et al. | 514/422 |
| 5,496,845 | 3/1996 | Martin et al. | 514/427 |

FOREIGN PATENT DOCUMENTS

| | | | |
|---|---|---|---|
| 0530147 | 3/1993 | European Pat. Off. | 548/561 |
| 0 771 526 A2 | 5/1997 | European Pat. Off. | |

OTHER PUBLICATIONS

Database WPI Section Ch, Week 9809, Derwent Publications Ltd., London, GB; Class C02, An 98–094646 XP002080819.

*Primary Examiner*—Floyd D. Higel
*Attorney, Agent, or Firm*—John W. Hogan, Jr.

[57] ABSTRACT

The present invention provides a method for the protection of wood, wood products and wooden structures from wood-eating insect attack and infestation which comprises treating said wood, wood product or wooden structure or the soil surrounding said wood, wood product or wooden structure with an insecticidally effective amount of an arylpyrrole compound of formula I.

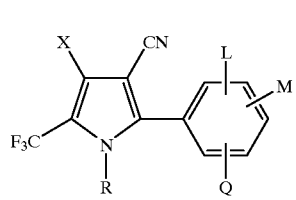

(I)

13 Claims, No Drawings

2-ARYL-4-HALO-5-(TRIFLUOROMETHYL) PYRROLE-3-CARBONITRILES FOR THE PROTECTION OF WOOD, WOOD PRODUCTS AND WOODEN STRUCTURES FROM INSECT ATTACK

This application claims priority from copending provisional application(s) Ser. No. 60/055,054 filed on Aug. 8, 1997.

BACKGROUND OF THE INVENTION

A broad class of arylpyrrole compounds and their insecticidal use in crop protection and animal health are described in U.S. Pat. Nos. 5,010,098; 5,310,938; and 5,455,263. It has now been found that a small select group of these arylpyrrole compounds are particularly useful for the protection of wood, wood products and wooden structures from infestation and attack by wood-eating insects such as termites, carpenter ants, wood-destroying beetles and the like, especially termites.

Termites are known to occur in virtually every state in the U.S., except Alaska, in all U.S. territories, and throughout the world in every continent except Antarctica. Termites cause extensive damage to wood, wood structures, wood products and cultivated plants and crops. They invade and damage poles, posts, timbers, lumber, buildings, shelters and the like. They are also destructive to cultivated plants and crops where they burrow into stems, tunnel out stalks and roots, and girdle the bark of trees. They eat grass and injure or damage field crops such as rubber, tea, coffee, cocoa, citrus and sugarcane.

Conventional methods to control termites have a common mechanism of action. This mechanism employs a chemical zone through which termites will not travel. This zone acts as a barrier by, either directly or indirectly, repelling the termites. However, while effective in repelling termites, conventional treatments cause very little, if any, effective control of the termite populations, as very few termites which encounter the barrier actually expire. Therefore, due to the minimal termite mortality and impact on termite foraging activity of conventional termite control methods, there remain vast populations of termites that continue to represent a significant threat to wood, wood products and wooden structures. In light of the limitations of conventional materials and methods to control termite populations, alternatives to those conventional methods for controlling these significantly destructive insects is highly desirable.

Therefore, it is an object of this invention to provide a highly effective method for the protection of wood, wood products and wooden structures from damage and destruction caused by infestation and attack by wood-eating insects such as termites, carpenter ants, wood-destroying beetles and the like, particularly termites.

It is a feature of this invention that the pressure and threat of destructive wood-eating insect populations, such as termite populations, may be significantly reduced.

Further objects and features of the invention will become apparent in the detailed description set forth below.

SUMMARY OF THE INVENTION

The present invention provides a method for protecting wood, wood products or wooden structures from wood-eating insect infestation which comprises treating said wood, wood product or wooden structure or the soil surrounding said wood, wood product or wooden structure with an insecticidally effective amount of an arylpyrrole compound of formula I

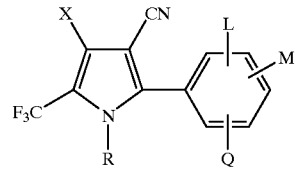

(I)

wherein R is hydrogen or $C_1$–$C_4$alkoxymethyl;
X is Cl or Br, and
L, M, and Q are each independently hydrogen, Cl, Br, I, F or $C_1$–$C_4$haloalkyl.

DETAILED DESCRIPTION OF THE INVENTION

Protecting wood, wood products and wooden structures from damage and destruction caused by wood-eating insects while effectively controlling the populations of said insects is a continuing scientific challenge. Conventional methods and materials such as organophosphates, pyrethroids, chlorinated hydrocarbons, and the like employ a common mechanism of action which is to essentially to form a chemical barrier which directly or indirectly repels the targeted wood-eating insects. Consequently, the wood-eating insect population size, and the pressure from said population, is not significantly reduced. Therefore, because these populations continue to persist in the targeted ecological environment, they continue to forage and, through trial and error, find gaps in the chemical barrier to gain access to the wood, wood product, or wooden structure meant to be protected. Further, in the case of subterranean wood-eating insect populations, post-treatment activities such as gardening, paving, remodeling, and the like may disturb the chemical barrier in the soil and create gaps that may be breached by the targeted subterranean wood-eating insects. Moreover, as the conventional materials degrade over time and become less effective as repellents, the largely uncontrolled populations of wood-eating insects can return to attack and infest the wood, wood product or wooden structure.

It has now been found that the select group of arylpyrrole compounds of formula I

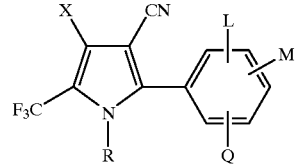

(I)

wherein R is hydrogen or $C_1$–$C_4$alkoxymethyl;
X is Cl or Br; and
L, M and Q are each independently hydrogen, Cl, Br, I, F or $C_1$–$C_4$haloalkyl;
is particularly useful for effectively and safely protecting wood, wood products and wooden structures from damage and destruction caused by attack or infestation by wood-eating insects such as termites, carpenter ants, wood-destroying beetles and the like, especially termites.

Advantageously, said compounds provide a non-repellent, slow-acting toxin useful for the control of pestiferous subterranean insects which imbibe or ingest soil for excavation or nutrition, especially termites. Said subterranean insects exchange nutrients between colony members; therefore, a slow-acting toxin allows sufficient time for one member to pass the toxin to another member before visible toxic effects are manifested. This slow action is particularly useful for the effective control of soil-dwelling, social, insect populations which are dependent upon a queen, such as carpenter ant populations. Further, since the select formula I arylpyrrole compounds are non-repellent, the targeted pestiferous insect colony members will continually travel through, attack or infest material which has been treated according to the method of invention, resulting in significant mortality, and control of said colony members, and concomittant reduction in pestiferous, wood-eating insect pressure.

Exemplary of the wood-eating insects included in the method of invention are: the economically important wood-destroying carpenter ants of the genus Camponotus, order Hymenoptera, family Formicidae such as *Camponotus pennsylvanicus, Camponotus abdominalis, Camponotus ferrugineus,* and the like; wood-destroying beetles such as powder post beetles which include the coleopteran families of Lyctidae, Ptinidae, Anobiidae and Bostrichidae, for example species such as *Lyctus planicollis, Anobium punctatum* and the like; and subterranean termites of the order Isoptera, including the families of Rhinotermitidae, Termitidae, Kalotermitidae and Hodotermitidae, examples of species include *Reticulitermes flavipes, Reticulitermes virginicus, Reticulitermes hesperus, Coptotermes formosanus,* and the like.

Surprisingly, the select formula I arylpyrrole compounds are highly effective for the protection of wood, wood products and wooden structures from the damage and destruction caused by the above-mentioned wood-eating insects, particularly termites.

Those particular arylpyrrole compounds of formula I preferred for use in the method of invention are those formula I compounds wherein R is $C_1$–$C_4$alkoxymethyl.

Another group of particular arylpyrrole compounds preferred for use in the method of invention is that group of compounds of formula I wherein L and Q are hydrogen and M is 4-Cl.

A third group of compounds of formula I especially useful in the method of the invention is that group wherein X is Br.

Exemplary of the select formula I arylpyrrole compounds which are useful in the inventive method are:
4-bromo-2-(p-chlorophenyl)-5-(trifluoromethyl)pyrrole-3-carbonitrile;
4-bromo-2-(p-chlorophenyl)-1-(ethoxymethyl)-5-(trifluoromethyl)pyrrole-3-carbonitrile;
4-chloro-2-(p-chlorophenyl)-5-(trifluoromethyl)pyrrole-3-carbonitrile;
4-chloro-2-(p-chlorophenyl)-1-(ethoxymethyl)-5-(trifluoromethyl)pyrrole-3-carbonitrile;
4-chloro-2-(p-chlorophenyl)-1-(methoxymethyl)-5-(trifluoromethyl)pyrrole-3-carbonitrile;
4-bromo-2-(p-chlorophenyl)-1-(methoxymethyl)-5-(trifluoromethyl)pyrrole-3-carbonitrile;
4-bromo-1-(ethoxymethyl)-5-(trifluoromethyl)-2-($\alpha,\alpha,\alpha$-trifluoro-p-tolyl)pyrrole-3-carbonitrile;
4-bromo-2-(3,4-dichlorophenyl)-1-(ethoxymethyl)-5-(trifluoromethyl)pyrrole-3-carbonitrile;
4-bromo-2-(2,4-dichlorophenyl)-1-(ethoxymethyl)-5-(trifluoromethyl)pyrrole-3-carbonitrile;
4-bromo-2-(3,5-difluorophenyl)-1-(ethoxymethyl)-5-(trifluoromethyl)pyrrole-3-carbonitrile;
4-bromo-2-(2,3-dichlorophenyl)-1-(ethoxymethyl)-5-(trifluoromethyl)pyrrole-3-carbonitrile;
4-bromo-2-(3,4-difluorophenyl)-1-(ethoxymethyl)-5-(trifluoromethyl)pyrrole-3-carbonitrile;
4-bromo-2-(3,5-dichlorophenyl)-1-(ethoxymethyl)-5-(trifluoromethyl)pyrrole-3-carbonitrile;
4-bromo-2-(3,4,5-trifluorophenyl)-1-(ethoxymethyl)-5-(trifluoromethyl)pyrrole-3-carbonitrile;
4-bromo-2-(3,4,5-trichlorophenyl)-1-(ethoxymethyl)-5-(trifluoromethyl)pyrrole-3-carbonitrile;
4-bromo-2-(2,5-dichlorophenyl)-1-(ethoxymethyl)-5-(trifluoromethyl)pyrrole-3-carbonitrile;
4-bromo-2-(2,6-dichlorophenyl)-1-(ethoxymethyl)-5-(trifluoromethyl)pyrrole-3-carbonitrile;
4-chloro-2-(3,4-dichlorophenyl)-1-(ethoxymethyl)-5-(trifluoromethyl)pyrrole-3-carbonitrile;
4-chloro-2-(3,5-dichlorophenyl)-1-(ethoxymethyl)-5-(trifluoromethyl)pyrrole-3-carbonitrile; or
4-chloro-1-(ethoxymethyl)-5-(trifluoromethyl)-2-($\alpha,\alpha,\alpha$-p-tolyl)pyrrole-3-carbonitrile.

Those compounds particularly useful in the method of the invention are: 4-bromo-2-(p-chlorophenyl)-1-(ethoxymethyl)-5-(trifluoromethyl)pyrrole-3-carbonitrile;
4-chloro-2-(p-chlorophenyl)-1-(ethoxymethyl)-5-(trifluoromethyl)pyrrole-3-carbonitrile;
4-bromo-2-(3,5-dichlorophenyl)-1-(ethoxymethyl)-5-(trifluoromethyl)pyrrole-3-carbonitrile;
4-bromo-2-(p-chlorophenyl)-5-(trifluoromethyl)pyrrole-3-carbonitrile; and
4-chloro-2-(p-chlorophenyl)-5-(trifluoromethyl)pyrrole-3-carbonitrile;

4-bromo-2-(p-chlorophenyl)-1-(ethoxymethyl)-5-(trifluoromethyl)pyrrole-3-carbonitrile is especially useful in the inventive method for protecting wood, wood products, and wooden structures from the damage and destruction caused by pestiferous subterranean wood-eating insects which imbibe or ingest soil for excavation or nutrition, such as termites, carpenter ants, or wood-destroying beetles, particularly termites.

In actual practice, wood such as lumber, wood products such as materials made from wood or cellulosic fibers and wooden structures may be protected from wood-eating insect infestation or damage, particularly termite infestation or damage, by spraying, dusting, drenching, soaking or impregnating said wood, wood product or wooden structure with a solution, emulsion, suspension, dust, powder, granule, or dispersion containing the select arylpyrrole compound of formula I. Wood, wood products or wooden structures may also be treated by drilling holes into same and filling the holes with a solution, emulsion, suspension or cellulosic bait composition containing the select arylpyrrole of formula I. The concentration of the formula I arylpyrrole compound in a dust, spray, drench, soak or impregnation treatment may be about 0.01% wt/wt to 10.0% wt/wt, preferably about 0.05% to 1.0% by weight.

In accordance with the method of invention, wood, lumber, wood chips and the like, wood products such as materials made from wood or cellulosic fibers and the like, and wooden structures may be protected from damage and destruction by wood-eating insects, particularly termites, by treating the soil surrounding said wood, wood product or wooden structure with a spray, dust, powder, granule, solution, emulsion, suspension or dispersion containing an effective amount of the select arylpyrrole compound of formula I. Rates of application of said arylpyrrole compound will vary according to prevailing environmental conditions such as wood-eating insect species, population density, weather conditions, soil type, vegetation growth, topographical characteristics, and the like. In general, rates of application of active ingredient sufficient to supply soil concentrations of about 1 ppm to 2,500 ppm, preferably about 25 ppm to 1,000 ppm may be effective.

For a more clear understanding of the invention, the following examples are set forth below. These examples are merely illustrative and are not understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

EXAMPLE 1

Evaluation of the Termiticidal Activity of Chlorfenapyr Over Time

For this evaluation, ten termites (*Reticulitermes virginicus*) are placed in a 5 cm petri dish containing a thin layer of moist soil which has been treated with an acetone solution of chlorfenapyr at various concentrations. (The acetone is evaporated before introduction of insects.) Observations of insect mortality are made at 8 hr. and 24 hr. after treatment. After 24 hr., all termites are removed from the treated soil and placed in 5 cm petri dishes containing non-treated soil and a strip of moistened cellulose filter paper as food supply. Observations of continued insect mortality are made daily for 7 days after exposure to the treated soil. The treatments are replicated 3 times. The data obtained are averaged and shown in Table I, below.

TABLE I

| Test Compound | Concentration (ppm) | % Mortality (Time After Treatment) | | |
|---|---|---|---|---|
| | | 8 hr. | 24 hr. | 7 days |
| Chlorfenapyr | 100 | 0 | 100 | 100 |
| Chlorfenapyr | 50 | 0 | 33.7 | 100 |
| Chlorfenapyr | 25 | 0 | 6.7 | 100 |
| Chlorfenapyr | 10 | 0 | 0 | 100 |
| Chlorfenapyr | 5 | 0 | 0 | 100 |
| Untreated Control | 0 | 0 | 0 | 0 |

Discussion

In this Example, the delayed-action mortality in termites exposed to the arylpyrrole compound is evident. There is no mortality after 8 hours of exposure to chlorfenapyr (Table I). However, after 24 hours the percentage of mortality increases. Further, over the next six days, even after the termites have been removed to untreated soil, mortality continues to increase. Ultimately, exposure to concentrations as low as 5 ppm chlorfenapyr causes 100% mortality.

EXAMPLE 2

Evaluation of the Termiticidal Activity of Test Compounds Over Time

In this evaluation, samples of test compound are dissolved in acetone and applied to a sandy loam soil in quantities sufficient to supply concentrations of 1,000, 100, 10 and 1 ppm by weight. Treated soil is then moistened with 5% by weight of water. The moistened, treated soil (5 g) is placed uniformly over the bottom of a 100×15 mm glass dish. Ten worker termites (Reticulitermes spp.) are placed on the treated soil and held for 7 days. Observations of moribundity are made daily. In this evaluation, moribundity is defined as ataxia, paralysis, or sluggishness. Moribund termites are recorded and removed daily. Each treatment is replicated 4 times. The data are averaged and shown in Table II, below.

TABLE II

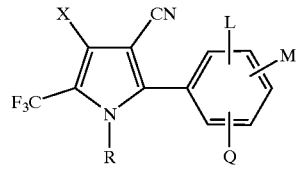

| Test Compound | | | | | Rate | % Moribundity | |
|---|---|---|---|---|---|---|---|
| R | X | L | M | Q | (ppm) | 1 DAT | 7 DAT |
| H | Br | H | 4-Cl | H | 1,000 | 100 | 100 |
| H | Br | H | 4-Cl | H | 100 | 46.7 | 100 |
| H | Br | H | 4-Cl | H | 10 | 3.2 | 75.6 |
| H | Br | H | 4-Cl | H | 1 | 10.0 | 16.7 |
| $CH_2OC_2H_5$ | Br | H | 4-Cl | H | 1,000 | 98.3 | 100 |
| $CH_2OC_2H_5$ | Br | H | 4-Cl | H | 100 | 19.2 | 100 |
| $CH_2OC_2H_5$ | Br | H | 4-Cl | H | 10 | 6.7 | 91.7 |
| $CH_2OC_2H_5$ | Br | H | 4-Cl | H | 1 | 5.0 | 49.4 |
| $CH_2OC_2H_5$ | Br | H | 4-Br | H | 1,000 | 96.7 | 100 |
| $CH_2OC_2H_5$ | Br | H | 4-Br | H | 100 | 98.3 | 100 |
| $CH_2OC_2H_5$ | Br | H | 4-Br | H | 10 | 11.7 | 100 |
| $CH_2OC_2H_5$ | Br | H | 4-Br | H | 1 | 10.0 | 43.3 |
| $CH_2OC_2H_5$ | Cl | H | 4-Cl | H | 1,000 | 100 | 100 |
| $CH_2OC_2H_5$ | Cl | H | 4-Cl | H | 100 | 100 | 100 |
| $CH_2OC_2H_5$ | Cl | H | 4-Cl | H | 10 | 26.4 | 100 |
| $CH_2OC_2H_5$ | Cl | H | 4-Cl | H | 1 | 1.7 | 86.7 |
| $CH_2OC_2H_5$ | Br | 3-Cl | H | 5-Cl | 1,000 | 100 | 100 |
| $CH_2OC_2H_5$ | Br | 3-Cl | H | 5-Cl | 100 | 90 | 100 |
| $CH_2OC_2H_5$ | Br | 3-Cl | H | 5-Cl | 10 | 3.3 | 96.8 |
| $CH_2OC_2H_5$ | Br | 3-Cl | H | 5-Cl | 1 | 3.3 | 36.7 |
| Untreated Control | | | | | 0 | 1.9 | 16.8 |

Discussion

The unique delayed-action mortality of the formula I arylpyrrole compound is demonstrated by the data shown in Table II of this Example. For instance, exposure to arylpyrrole compounds at concentrations of 10 ppm causes little moribundity after 24 hours (3.2% to 26.4%). However, after 7 days exposure, significant moribundity (75.6% to 100%) results for all of these compounds.

EXAMPLE 3

Evaluation of Termiticidal Activity of Chlorfenapyr on a Variety of Species

In this evaluation, moist soil is treated with a gradient dilution of a 2SC formulation of chlorfenapyr as described in U.S. Pat. No. 5,496,845. Groups of 10 termites are placed in a 5 cm petri dish containing a thin layer of the treated soil. Observations of insect mortality are made at 8 hr. and 24 hr. after treatment. After 24 hr., all termites are removed from the treated soil and placed in petri dishes containing non-treated soil and a strip of moistened cellulose filter paper as food. Insect mortality observations are made daily, for 7 days after exposure to the treated soil. Each treatment is replicated 6 times. The data are averaged and shown in Table III, below.

TABLE III

| | | % Mortality at 7 DAT | | | |
| --- | --- | --- | --- | --- | --- |
| Test Compound | Rate (ppm) | Reticulitermes flavipes | Reticulitermes virginicus | Reticulitermes hesperus | Coptotermes formosanus |
| Chlorfenapyr | 1000 | 96.7 | 86.7 | 100 | 96.7 |
| Chlorfenapyr | 500 | 90.0 | 78.3 | 100 | 98.3 |
| Chlorfenapyr | 100 | 18.3 | 16.7 | 22.5 | 43.3 |
| Chlorfenapyr | 50 | 8.3 | 20.0 | 20.0 | 36.7 |
| Chlorfenapyr | 10 | 3.3 | 16.7 | 10.0 | 23.3 |
| Untreated Control | 0 | 6.7 | 0 | 5.0 | 10.0 |

Discussion

In this Example wherein all of the major species of subterranean termites in the U.S. are studied, the data in Table III clearly demonstrate that all termite species tested are equally susceptible to the lethal effects of the formula I arylpyrrole compound.

EXAMPLE 4

Comparative Evaluation of Non-Repellency and Efficacy of Formula I Arylyrrole Compounds and Pyrethroid Compounds in the Soil A sandy loam soil is treated with acetone solutions of either chlorfenapyr or permethrin to obtain concentrations of 100, 10, or 1 ppm. Untreated soil is used for the controls. After treatments have dried, enough treated soil is transferred into 15 cm lengths of transparent plastic tubing (1.5 cm diam.) to form a column of treated soil 5 cm in length. A 1 cm thick 6% agar plug is fitted at each end of the 5 cm column of soil. Several pieces of woodflour (food source) are placed in one end which, when the tube is inverted, is situated beneath the treated-soil column. Thirty (30) termites (*Reticulitermes flavipes*) are then introduced into the top open end of the plastic tubing opposite the food source. Both ends of the tubing are sealed, to form a "test". Test units are held at room temperature, in the dark, for the duration of the study. After 1 day and 3 days, measurements are taken of the distance the termites tunnel into the 5 cm column of treated soil. Each concentration is replicated 4 times for each test compound. At the conclusion of the experiment, the test units are destructively sampled to determine termite mortality.

TABLE IV

| Test Compound | Rate (ppm) | Depth in cm of termite penetration (% of 5 cm) | | | % Mortality |
| --- | --- | --- | --- | --- | --- |
| | | 1 dat | | 3 dat | 3 dat |
| chlorfenapyr | 100 | 4.4 | (88%) | 5.0 (100%) | 93.0% |
| | 10 | 3.8 | (76%) | 5.0 (100%) | 46.0% |
| | 1 | 5.0 | (100%) | 5.0 (100%) | 33.0% |
| permethrin | 100 | 0.0 | (0%) | 0.0 (0%) | 7.0% |
| | 10 | 0.1 | (2%) | 0.2 (4%) | 0.0% |
| | 1 | 1.2 | (24%) | 2.6 (52%) | 17.0% |
| untreated control | 0 | 3.3 | (66%) | 5.0 (100%) | 20.0% |

Discussion

In Table IV, repellency is clearly demonstrated for the pyrethroid compound, permethrin. There is very little penetration by the termites into the permethrin treated soil column, especially at rates of 100 or 10 ppm. As can be seen, few termites died from exposure due to the repellency of permethrin. Even at 1 ppm concentration of permethrin when termites penetrated through more than 50% of the treated soil column, mortality did not differ from that observed in the untreated control. In contrast, the formula I arylpyrrole compound, chlorfenapyr, clearly demonstrated non-repellency. At all three concentrations of chlor-fenapyr, the termites rapidly penetrated the treated soil column. Further, exposure to the chlorfenapyr in the treated soil columns proved lethal to the termites. Even at the lowest concentration tested (1 ppm), exposure to chlorfenapyr caused higher mortality in termites than did exposure to the same 1 ppm concentration of permethrin.

EXAMPLE 5

Evaluation of Non-Repellency and Efficacy of Test Compounds in the Soil

In this evaluation, 300 termites (Reticulitermes flavipes) are added to a 5 cm-round tubular container filled with a sand/vermiculite substrate and containing a small, pre-weighed pine block (unprotected wood). This container is connected with a 7 cm length of 3 mm plastic tubing to a second container filled with a sandy loam soil which has been treated with a test compound. At the opposite end of the second container is connected, by plastic tubing, a third container in which is placed a single pre-weighed block of pine wood (protected wood). Termites must tunnel through the treated soil in order to access the "protected" block of pine wood. After 5 weeks, the termites from all containers are removed, % insect mortality is determined and the pine blocks are weighed. The treatments are replicated 6 times. The data is averaged and shown in Table V below.

TABLE V

| Test Compound | Rate (ppm) | % Mortality | Consumption of Unprotected Wood | Consumption of Protected Wood |
| --- | --- | --- | --- | --- |
| Chlorfenapyr | 1000 | 100 | 36 mg | 16 mg |
| Chlorfenapyr | 500 | 99.4 | 52 mg | 37 mg |
| Chlorfenapyr | 100 | 93.4 | 308 mg | 75 mg |
| Chlorfenapyr | 50 | 87.7 | 625 mg | 133 mg |
| Chlorfenapyr | 10 | 44.5 | 833 mg | 625 mg |
| Untreated Control | 0 | 29.0 | 900 mg | 842 mg |

In this Example, the data in Table V demonstrate the advantages of the non-repellence of an arylpyrrole compound, chlorfenapyr. In the absence of chlorfenapyr residues in the soil in the middle container, termites consume equal quantities of wood from both ends of the test chamber. However, in all tests where the soil in the middle container is treated with chlorfenapyr, significantly less wood is consumed from the protected pine block than is consumed from the unprotected pine block. In this study the percentage mortality is consistently $\leq 85\%$ at soil concentrations as low as 50 ppm.

What is claimed is:

1. A method for protecting wood, wood products or wooden structures from wood-eating insect infestation which comprises treating said wood, wood product or wooden structure or the soil surrounding said wood, wood product or wooden structure with a wood-eating insecticidally effective amount of an arylpyrrole compound of formula I

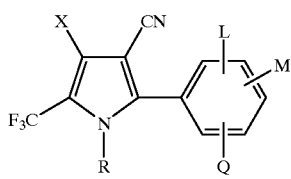

(I)

wherein R is hydrogen or $C_1$–$C_4$alkoxymethyl;
X is Cl or Br, and
L, M, and Q are each independently hydrogen, Cl, Br, I, F or $C_1$–$C_4$haloalkyl;
wherein said arylpyrrole compound is applied essentially in the absence of a pyrethroid.

2. The method according to claim 1 wherein said wood-eating insect is selected from the group consisting of termites, carpenter ants and wood-destroying beetles.

3. The method according to claim 2 wherein said insects are termites.

4. The method according to claim 1 wherein the wood or wood product is treated with an insecticidally effective amount of said arylpyrrole compound by drench, soak or impregnation.

5. The method according to claim 4 wherein said wood or wood product is treated by impregnation.

6. The method according to claim 1 wherein the soil is treated with an arylpyrrole compound of formula I at a concentration of about 1.0 ppm to 2500 ppm.

7. The method according to claim 6 wherein the soil is treated with an arylpyrrole compound of formula I at a concentration of about 25 ppm to 1000 ppm.

8. The method according to claim 1 having a formula I arylpyrrole compound wherein R is $C_1$–$C_4$-alkoxymethyl.

9. The method according to claim 1 wherein L and Q are hydrogen and M is 4-Cl.

10. The method according to claim 1 wherein X is Br.

11. The method according to claim 1 wherein the formula I arylpyrrole compound is selected from the group consisting of: 4-bromo-2-(p-chlorophenyl)-5-(trifluoromethyl)pyrrole-3-carbonitrile;
4-bromo-2-(p-chlorophenyl)-1-(ethoxymethyl)-5-(trifluoromethyl)pyrrole-3-carbonitrile;
4-chloro-2-(p-chlorophenyl)-5-(trifluoromethyl)pyrrole-3-carbonitrile;
4-chloro-2-(p-chlorophenyl)-1-(ethoxymethyl)-5-(trifluoromethyl)pyrrole-3-carbonitrile;
4-chloro-2-(p-chlorophenyl)-1-(methoxymethyl)-5-(trifluoromethyl)pyrrole-3-carbonitrile;
4-bromo-2-(p-chlorophenyl)-1-(methoxymethyl)-5-(trifluoromethyl)pyrrole-3-carbonitrile;
4-bromo-1-(ethoxymethyl)-5-(trifluoromethyl)-2-(α, α,α-trifluoro-p-tolyl)pyrrole-3-carbonitrile;
4-bromo-2-(3,4-dichlorophenyl)-1-(ethoxymethyl)-5-(trifluoromethyl)pyrrole-3-carbonitrile;
4-bromo-2-(2,4-dichlorophenyl)-1-(ethoxymethyl)-5-(trifluoromethyl)pyrrole-3-carbonitrile;
4-bromo-2-(3,5-difluorophenyl)-1-(ethoxymethyl)-5-(trifluoromethyl)pyrrole-3-carbonitrile;
4-bromo-2-(2,3-dichlorophenyl)-1-(ethoxymethyl)-5-(trifluoromethyl)pyrrole-3-carbonitrile;
4-bromo-2-(3,4-difluorophenyl)-1-(ethoxymethyl)-5-(trifluoromethyl)pyrrole-3-carbonitrile;
4-bromo-2-(3,5-dichlorophenyl)-1-(ethoxymethyl)-5-(trifluoromethyl)pyrrole-3-carbonitrile;
4-bromo-2-(3,4,5-trifluorophenyl)-1-(ethoxymethyl)-5-(trifluoromethyl)pyrrole-3-carbonitrile;
4-bromo-2-(3,4,5-trichlorophenyl)-1-(ethoxymethyl)-5-(trifluoromethyl)pyrrole-3-carbonitrile;
4-bromo-2-(2,5-dichlorophenyl)-1-(ethoxymethyl)-5-(trifluoromethyl)pyrrole-3-carbonitrile;
4-bromo-2-(2,6-dichlorophenyl)-1-(ethoxymethyl)-5-(trifluoromethyl)pyrrole-3-carbonitrile;
4-chloro-2-(3,4-dichlorophenyl)-1-(ethoxymethyl)-5-(trifluoromethyl)pyrrole-3-carbonitrile;
4-chloro-2-(3,5-dichlorophenyl)-1-(ethoxymethyl)-5-(trifluoromethyl)pyrrole-3-carbonitrile; and
4-chloro-1-(ethoxymethyl)-5-(trifluoromethyl)-2-(α,α,α-p-tolyl)pyrrole-3-carbonitrile.

12. The method according to claim 11 wherein said arylpyrrole compound is selected from the group consisting of: 4-bromo-2-(p-chlorophenyl)-1-(ethoxymethyl)-γ-(trifluoromethyl)pyrrole-3-carbonitrile;
4-chloro-2-(p-chlorophenyl)-1-(ethoxymethyl)-5-(trifluoromethyl)pyrrole-3-carbonitrile;
4-bromo-2-(3,5-dichlorophenyl)-1-(ethoxymethyl)-5-(trifluoro-methyl)pyrrole-3-carbonitrile;
4-bromo-2-(p-chlorophenyl)-5-(trifluoromethyl)pyrrole-3-carbonitrile; and
4-chloro-2-(p-chlorophenyl)-5-(trifluoromethyl)pyrrole-3-carbonitrile.

13. The method according to claim 12 wherein said arylpyrrole compound is 4-bromo-2-(p-chlorophenyl)-1-(ethoxymethyl)-5-(trifluoromethyl)pyrrole-3-carbonitrile.

* * * * *